United States Patent [19]
Schimmelpfennig

[11] Patent Number: 5,878,154
[45] Date of Patent: *Mar. 2, 1999

[54] METHOD AND APPARATUS FOR IMAGE RECOGNITION FOR BLIND AND SEVERELY VISUALLY HANDICAPPED PERSONS

[76] Inventor: Winfried Schimmelpfennig, Bornberg 12, D-18292 Krakow am See, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 640,958

[22] Filed: May 10, 1996

[30] Foreign Application Priority Data

Nov. 12, 1993 [DE] Germany .......................... 43 39 237.7

[51] Int. Cl.$^6$ ....................................... A61F 9/08
[52] U.S. Cl. ............................... 382/114; 341/21; 348/62; 382/128; 134/434; 623/4
[58] Field of Search ........................... 340/407.1, 825.19; 341/21, 31; 345/108, 110; 348/61, 62; 382/114; 434/112–114; 607/143; 623/4, 66

[56] References Cited

U.S. PATENT DOCUMENTS

| | | |
|---|---|---|
| 3,612,061 | 10/1971 | Collins et al. ........................... 607/148 |
| 3,766,311 | 10/1973 | Boll ............................................ 348/62 |
| 4,972,501 | 11/1990 | Horyu ...................................... 382/114 |

FOREIGN PATENT DOCUMENTS

| | | |
|---|---|---|
| 326283 | 9/1920 | Germany . |
| 2330403 | 1/1975 | Germany . |

OTHER PUBLICATIONS

Collins, C.C., A Microcomputer Based Blind Mobility Aid, Frontiers of Engineering and Computing in Health Care – 1984. Proceedings —Sixth Annual Conference of the IEEE Engineering in Medicine and Biology Society, pp. 52–55, Sep. 1984.

Jarmul et al., Investigation of Significant Interface Parameters Involved in the Electromechanical Transfer of Tactile Information, Proceedings of the Fifteenth Annual Northeast Bioengineering Conference, IEEE, pp. 43–44, Mar. 1989.

Kaczmarek et al., A Tactile Vision–Substitution System for the Blind: Computer–Controlled Partial Image Sequencing, IEEE Transactions on Biomedical Engineering, pp. 602–660, Aug. 1985.

Collins, C.C. Tactile Television–Mechanical and Electrical Image Projection, IEEE Transactions on Man–Machine Systems, Mar. 1970

Heller et al., Determining Reading and Writing Media for Individuals with Visual and Physical Impairments, Journal of Visual Impairment and Blindness, pp. 162, Mar. 1998.

IIBM Technical Disclosure Bulletin, vol. 32, No. 12, pp. 445–447, May 1990.

*Primary Examiner*—Amelia Au
*Assistant Examiner*—Marc Bobys
*Attorney, Agent, or Firm*—Jordan and Hamburg LLP

[57] ABSTRACT

An apparatus enables the blind and the severely visually handicapped to recognize images by way of the tongue. Optical image information, in the form of video images, is processed electronically and transferred as an image representation to flat monitor matrix which is worn in the oral cavity in the tactile region of the tongue. Electrical current density, temperature or relief images are used to create the representations, whereby the images can be scanned by the tongue and recognized. High image resolution is attainable over the matrix region, and the tip of the tongue can be concentrated on any image detail, thus approximating sharp vision perceived by the normal eye.

8 Claims, 1 Drawing Sheet

METHOD AND APPARATUS FOR IMAGE RECOGNITION FOR BLIND AND SEVERELY VISUALLY HANDICAPPED PERSONS

BACKGROUND OF THE INVENTION

The invention relates to a method, with which perception of the contents of an image becomes possible for the blind and for persons, whose vision is highly impaired. The invention also relates to an apparatus for carrying out the method.

According to the known state of the art, which is documented by the German Offenlegungsschrift 23 30 403, there are visual aids for the blind, which project electrical potential images with the help of an electrode matrix directly from the image source onto the skin of the forehead or a finger. Since the electrical resistance of the skin must be overcome, appreciable electrical voltages, which are harmful in the long run, are required at these electrodes and undesirable galvanic and thermal side effects occur and the spatial resolution is very slight, so that one cannot actually speak of true image recognition.

It is an object of the invention to make available for a blind or visually impaired person an aid for image recognition and orientation within his surroundings, in that his limited optical perception capabilities are compensated for by technical aids in cooperation with other operative sensing organs of the impaired.

Pursuant to the invention, this objective is accomplished by a method, which comprises the following steps. First, optically detecting an image content by an image detection device used by a visually impaired person. Second, computer-aided processing image information from the image detection device. Third, transferring processed image information to a monitor matrix, worn in a scanning region of the tongue of the impaired person for representing associated image structures. Finally, scanning image structures produced by the monitor matrix by means of the tongue of the impaired person and, with that, effecting sensory detection of the image content and/or control of computer parameters by action upon sensors in the monitor matrix, by means of the tongue of the impaired person.

In an embodiment of the invention, signals for representing image information, which are processed electronically, are transferred to a flat monitor matrix, which can be worn in the oral cavity in the tactile region of the tongue. Potential distribution images, temperature distribution images or relief images are used as representation principles by the flat monitor matrix.

A feature of the present invention includes for generating an electrical current density image, the actuators of the matrix consisting of electrode pairs contacted by line and column leads, and each image point being assigned to a local current flow within an individual electrode pair.

According to a further distinguishing feature of the invention, the monitor matrix has sensors, which detect the position of the tip of the tongue on the monitor matrix for controlling computer parameters.

DETAILED DESCRIPTION OF THE INVENTION

Figure 1:
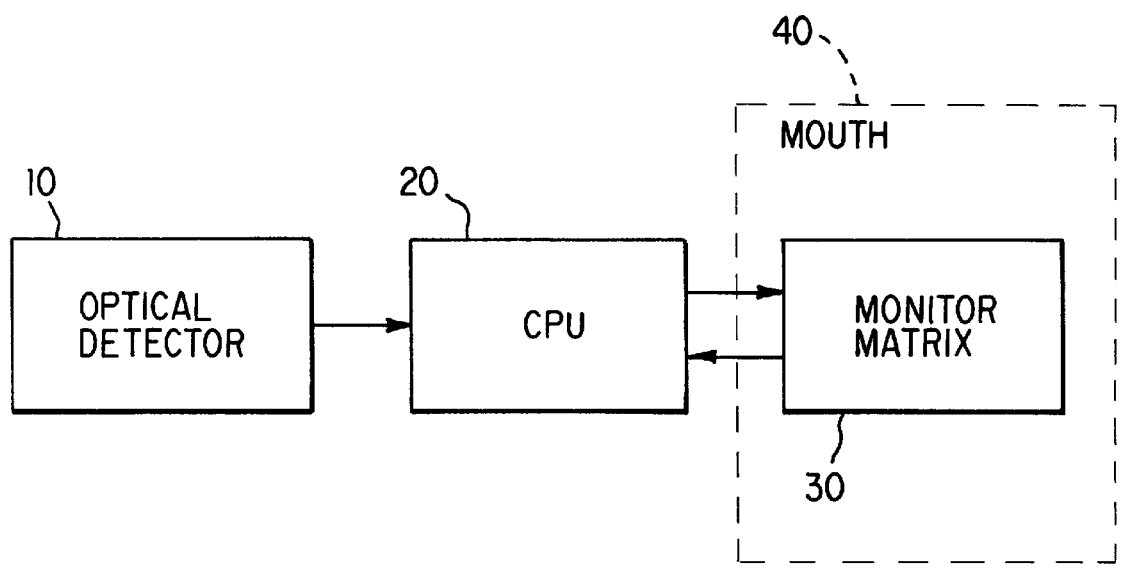
FIG. 1 is a block diagram of the apparatus of the present invention.

Referring to FIG. 1 the inventive apparatus for implementing the method of the present invention consists of an optical image detection means 10, which can be used by the impaired person for the optical detection of image content, a computer (CPU) 20, which can be used by the impaired person for processing image information from the image detected, a transfer means for transferring the processed image information, a monitor matrix 30 worn in the scanning region of the tongue of the impaired person for representing image structures assigned to the pictorial content and/or sensors, which are integrated into the monitor matrix 30 and can be acted upon by the tongue of the impaired person for controlling computer parameters.

The invention is described in greater detail by means of an example of a system, with which a blind person uses the tongue to scan image structures represented on an active surface of the monitor matrix 30 worn in the mouth 40. The active surface is constructed as a matrix and, in conjunction with the optical detector 10 in the form of a tiny video camera carried by the impaired person and the microcomputer 20, can function as a complete orientation aid for a blind person together with other sensory organs to, for the first time, effectively replace the optical perception of the eye.

Figure 2:
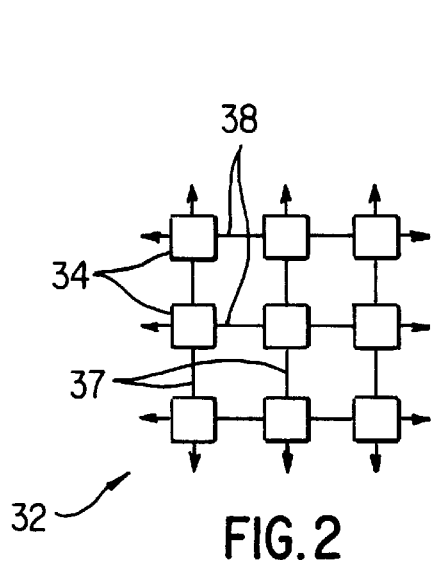
FIG. 2 is a schematic diagram of a monitor matrix of the present invention.
Figure 3A:
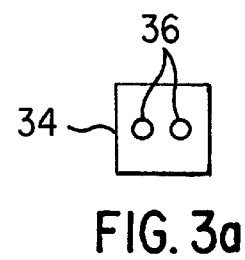
FIG. 3a is a schematic diagram of a first embodiment of an actuator of the present invention.
Figure 3B:
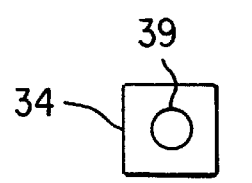
FIG. 3b is a schematic diagram of a second embodiment of an actuator of the present invention.

Referring to FIGS. 2–3b, the monitor matrix 30 is a special matrix in the form of a dental brace adapted to the shape of the mouth, which is placed in the mouth 40. Image structures, which are supplied by the video camera and processed by the computer 20 is reproduced on the monitor matrix 30. The point grid representations on the monitor matrix 30 are scanned as a whole by the tongue and in detail by the tip of the tongue.

The images are transformed either into current density distributions, temperature distributions or relief images, depending on the construction of the individual punctiform actuators 34 of the matrix. Since any video signals, such as TV signals or computer images, can be coupled in as input signals, an effective visual aid is provided and significant rehabilitation results in many applications.

In practice, starting out from the signal flow, a constant improvement in and expansion of fields of application of the system are achieved by exchanging and optimizing individual modules provided by a systematic, modular construction of the system from recording the image the computerized processing of the image, the stabilization, the filtering and the enhancement of contrast up to the measurement of the signal and its representation on the monitor matrix 30.

Compared to the known state of the art, the inventive image recognition by way of the tongue for the first time opens up the possibility of concentrating on a matrix with many thousands of image points, specially developed for this application, by way of the tip of the tongue on any detail of the image, scanning the part of the matrix more accurately to analyze image content. In persons with vision, this corresponds to the principle of the eye "looking at something", since the eye also has acute vision only over a small region. As a result, the blind experience a significant increase in spatial image resolution over the whole of the matrix region.

Since the very sensitive and highly resolving tip of the tongue is used to scan the image, the total energy required by the whole monitor matrix 30 is less by orders of magnitude than in other devices. Therefore, despite the relatively high number of image points, harmful side effects and dimensions are minimized so that the matrix monitor matrix 30 can be worn unobtrusively similar to a dental prosthesis.

The matrix for the potential image representation has a height of about 20 mm and a width of about 40 mm. Its top surface is adapted to the shape of the palate of the user. The matrix has modified electrode pairs 36, contacted in columns 37 and lines 38. The whole surface of the matrix is polished so that the tongue cannot mechanically detect the arrangement of the electrode pairs, and thus is not irritated. An electric current density image is projected onto the electrode pairs, causing every individual image point to act for the tongue as a tiny mechanical obstacle, which cannot be wiped away; intuitively, the impression of a relief image is obtained, which can be scanned broadly with the tongue surface and in detail with the tip of the tongue. Galvanic effects are completely suppressed by a special, potential-free alternating signal form. Due to the triggering of the electrode pairs, only a locally limited short current path is generated for each image point; the matrix, as a whole, remains electrically neutral with respect to the oral cavity. Alternatively, the actuator is provided with a thermal or micromechanical element 39 to provide a thermal or relief image representation.

I claim:

1. An image-recognition method for one of a blind and highly visually impaired person, the method comprising the following steps:

optically detecting an image using an image detection device for converting said image into digital signals containing image information;

processing the image information gained from the image detection device using a computer to produce processed image information;

transferring the image information to a monitor matrix for reproducing image structure representative of said image using non-optical means for producing a plurality of image points permitting detection by the tongue of the impaired person when scanned thereby;

wearing the monitor matrix in an oral cavity region accessible for scanning by the tongue of the impaired person; and scanning said image structure in detail with a tip of the tongue of the impaired person and broadly with a surface of the tongue, thereby effecting sensory detection of said image in a manner mimicking normal eye function and providing the impaired person with enhanced spacial image resolution over a whole of said monitor matrix by permitting said impaired person to accurately analyze area portions of said image information from said image structure.

2. An apparatus for use by a visually impaired person, the apparatus comprising:

an image detection means for optically detecting image content of a surroundings;

a computer for processing image information representative of said detected image content;

transfer means for transferring processed image information from said computer; and a monitor matrix, for wearing by the impaired person in an oral cavity region accessible within a scanning region of a tongue of the impaired person, for representing in the form of a plurality of image points said image content using said processed image information from said transfer means, there being a density of said plurality of image points sufficient to permit scanning of a detail portion of said monitor matrix with a tip of the tongue, and permitting broad scanning by a surface of the tongue of the impaired person, thereby effecting sensory detection of said image in a manner mimicking normal eye function and providing the impaired person with enhanced spacial image resolution over a whole of said monitor matrix by permitting the impaired person to accurately analyze area portions of said image content by scanning the detail portion of said monitor matrix with the tip of the tongue, and scanning said monitor matrix broadly with the surface of the tongue.

3. An apparatus according to claim 2 wherein:

said monitor matrix includes means for representing in the form of the plurality of image points said image content using said processed image information from said transfer means;

said means for representing including a grid of punctiform actuators configured to permit scanning by the tongue of the visually impaired person, each actuator of said grid being driven by a pair of inputs; and said transfer means including electrically conductive discrete columns and lines through which processed image information is transferred to said actuators, and respective ones of said columns and lines being connected to a corresponding one input of said pair of inputs.

4. The apparatus of claim 3, wherein each of said actuators includes an electrode pair, each electrode of said electrode pair being driven by a respective one of said discrete columns and lines, for generating an electric current density image comprised of local current flow between electrode pairs of energized ones of said actuators.

5. The apparatus of claim 3, wherein said actuators include quasi punctiform electrical heating elements, which arise as nodal points between said discrete columns and lines, for generating a temperature image representative of said image content.

6. The apparatus of claim 3, wherein each of the actuators includes a micromechanical image point element for generating a relief image of said image content.

7. The apparatus of claim 2, further including sensors, which can be acted upon by the tongue of the visually impaired person, in said monitor matrix for controlling computer parameters.

8. The apparatus of claim 4, wherein a surface of said monitor matrix is polished.

* * * * *